United States Patent [19]
Fain et al.

[11] Patent Number: 5,679,026
[45] Date of Patent: Oct. 21, 1997

[54] HEADER ADAPTER FOR AN IMPLANTABLE CARDIAC STIMULATION DEVICE

[75] Inventors: Eric S. Fain, Menlo Park; Timothy A. Fayram, Gilroy, both of Calif.

[73] Assignee: Ventritex, Inc., Sunnyvale, Calif.

[21] Appl. No.: 577,593

[22] Filed: Dec. 21, 1995

[51] Int. Cl.⁶ .................................................. H01R 25/00
[52] U.S. Cl. ........................... 439/651; 439/909; 607/37
[58] Field of Search ...................................... 439/651, 909, 439/652, 175; 607/2, 5, 27, 36, 37, 38, 9, 115, 119

[56] References Cited

U.S. PATENT DOCUMENTS

| | | | |
|---|---|---|---|
| 4,628,934 | 12/1986 | Pohndorf et al. | 128/419 |
| 5,000,177 | 3/1991 | Hoffmann et al. | 607/2 |
| 5,007,864 | 4/1991 | Stutz, Jr. | 439/651 |
| 5,314,452 | 5/1994 | Hirschberg et al. | 607/37 |
| 5,470,346 | 11/1995 | Adams | 607/37 |

Primary Examiner—David L. Pirlot
Assistant Examiner—Tho D. Ta
Attorney, Agent, or Firm—Steven M. Mitchell; Mark J. Meltzer

[57] ABSTRACT

A header adapter which is a separately molded part and which is designed to be secured to receiving portions of the header and pulse generator case of an implantable cardiac stimulation device, such as a pacemaker or implantable cardioverter-defibrillator, in order to provide a different lead connector port configuration than that provided by the header of the device. The header adapter has a plurality of adapter lead connector ports and a plurality of lead connectors affixed to a rear portion (mounting side) thereof. The lead connectors extend outwardly from the rear portion of the header adapter, and are insertable into corresponding lead connector ports of the header of the implantable cardiac stimulation device to which the header adapter is to be secured. At least one of the plurality of adapter lead connector ports is of a different size than any of the header lead connector ports of the device to which the header adapter is to be secured, and/or the number of adapter lead connector ports is different (greater or less than) the number of header lead connector ports of the device to which the header adapter is to be secured. Two or more leads inserted into the header adapter lead connector ports can be electrically connected to the same lead connector and/or one or more of the leads inserted into a header adapter lead connector port(s) can each be electrically connected to two or more of the lead connectors. Further, one or more of the lead connectors can be an electrically inactive "dummy" lead connector. The header adapter is preferably made of a transparent or translucent polymeric or other electrically insulative, biocompatible material, such as an epoxy resin or a thermoplastic elastomer. The invention also relates to an implantable cardiac stimulation device to which the header adapter is secured.

28 Claims, 3 Drawing Sheets

HEADER ADAPTER FOR AN IMPLANTABLE CARDIAC STIMULATION DEVICE

BACKGROUND OF THE INVENTION

The present invention relates generally to the field of implantable cardiac stimulation devices, and more particularly, to a header adapter which is designed to fit onto the header and case of an implantable cardiac stimulation device in order to provide a different lead connector port configuration than is provided by the header of the implantable cardiac stimulation device.

Various types of implantable cardiac stimulation devices are presently available for delivering various types of cardiac stimulation therapy. The two most common types which are in widespread use are pacemakers and implantable cardioverter-defibrillators (ICDs). Pacemakers generally produce relatively low voltage pacing pulses which are delivered to the patient's heart through low voltage, "bipolar" pacing leads, generally across spaced-apart ring and tip electrodes thereof which are of opposite polarity. These pacing pulses assist the natural pacing function of the heart in order to prevent bradycardia. Contemporary ICDs are capable of delivering tiered therapy, e.g., anti-bradycardia pacing therapy, anti-tachycardia pacing therapy, cardioversion therapy, and defibrillation therapy. Each tier or level of therapy requires the delivery of pulses of progressively higher voltage.

Early generation ICDs utilized a lead system which consisted of at least one epicardial patch electrode of a first polarity which was sewn onto the surface of the patient's heart, in combination with another epicardial patch electrode of a second polarity or a transvenous electrode of a second polarity placed in the patient's superior vena cava above the right atrium of the patient's heart. A thoracotomy procedure (i.e., a surgical opening of the patient's chest) was required to implant the epicardial patch electrodes.

Fortunately, lead systems have been developed which eliminate the necessity of a thoracotomy. Although there are a variety of different such nonthoracotomy lead systems which are presently known, most contemporary systems utilize a combination of a right ventricular (RV) endocardial lead electrode placed in the apex of the right ventricle of the patient's heart, a superior vena cava (SVC) transvenous lead electrode placed adjacent the sino-atrial node of the patient's heart, and, if necessary, a subcutaneous (SQ) electrode (located underneath the patient's skin in the area of the left chest wall). Of course, at least two of these "unipolar" lead electrodes are of opposite polarity.

In general, the header of an ICD is provided with a plurality of lead connector cavities or ports into which the implanting physician (or other medical personnel) can insert corresponding lead connectors of the leads which are required to provide the electrode configuration which optimizes the therapy delivered by the ICD for a given patient. After inserting the lead connectors of the appropriate leads into the corresponding lead connector ports provided in the header of the ICD, the implanting physician tightens set screws into corresponding transversely disposed set screw cavities and electrical connector blocks provided in the header onto the lead connector pins of the corresponding lead connectors of the inserted leads, so that the set screws are in firm, stable contact with the corresponding lead connector pins. The electrical connector blocks are electrically connected to the output voltage terminals of the pulse generator circuitry contained in the housing of the ICD, so that when the set screws are tightened down onto the lead connector pins, the inserted lead electrodes are electrically coupled to the output of the ICD.

Unfortunately, prior to 1993 there were no standards for lead connectors and connector ports used in ICD systems. Each manufacturer developed its own design for the lead connectors and connector ports. This made use of leads from one manufacturer with the ICD of another manufacturer difficult. Some manufacturers provided different models of their ICD having different headers with connector ports designed to fit and interface with the lead connectors of various other manufacturers. An implanting physician could choose the ICD with the header which at least minimized the need for adapters. An alternative approach has been to utilize a lead adapter for each lead connector or those of the lead connectors which were not of the correct size or configuration to fit the connector ports. However, these adapters are bulky and have tended to be one of the least reliable elements in the system. While this problem has been somewhat alleviated with the adoption of industry standards for lead connectors and connector ports, the problem still exists where a replacement ICD is implanted in a patient having non-standard leads since the leads are generally expected to remain implanted in each patient for the remainder of their life. The replacement ICD may not be able to accommodate the original lead configuration. It may also be a problem where a patient has defibrillation leads from one manufacturer and pacing/sensing leads from another manufacturer.

Another possible problem with the continual drive to reduce the size of implantable devices is that the standards may change to provide for smaller devices and lead connectors.

The header of an ICD or other implantable cardiac device is usually made by molding a transparent or translucent polymeric material in situ onto the case or can which houses the pulse generator circuitry of the device. An alternative assembly method utilized a header that is molded separately and it is attached to the case or can using a compliant adhesive. Suitable header materials include epoxy resin, thermoplastic elastomers and other electrically insulative, biocompatible materials. The manufacture of a number of different device models each having a different type of header (i.e., one which provides a different lead connector port configuration) necessitates a different in situ or separate molding process to form the header of each device model. This requirement intrinsically increases the complexity (and thus, the cost) of the device manufacturing process. Moreover, because the requirement of different in situ or separate molding processes for different header/model types increases the number of variables in this step of the device manufacturing process, the risk (statistical probability) that an error will occur in this step of the device manufacturing process is likewise increased, thereby reducing the efficiency and reliability of the device manufacturing process. In the case of the in situ molding process, the forming of the header is usually the last step (or nearly the last step) in the device manufacturing process. Consequently, if the header is not formed properly (i.e., does not meet exacting specifications), then the entire device may have to be discarded, thereby reducing the effective yield of the device manufacturing process, and thus, the per unit cost of the devices. Furthermore, some types of headers are more difficult to make than others, thereby resulting in a lower yield and higher per unit cost for the corresponding device models. As such, making a single device model which has a header of the type which is the simplest to manufacture would reduce the cost and complexity of the device manufacturing process.

While manufacturing a single device model having a single type header which is the simplest type to make would optimize the efficiency and reliability of the device manufacturing process, it would require that many replacement devices utilize numerous individual adapters to connect the patient's existing lead system to the new device. First, the implanting physician or other medical personnel must insert the adapter(s) into the appropriate lead connector port(s). Second, a sufficient supply of different-sized adapters must be readily available to the implanting physician at the time of device implantation. Third, and most importantly, presently available adapters are prone to insulation and conductor failures as a result of the mechanical stresses to which they are subjected during the life of the device. This stress-induced failure of the adapters can cause dangerous malfunctioning of the system including nondetection of arrhythmias, inappropriate therapy delivery and therapy failure, and thus, failure of the adapters presents a significant safety hazard.

Based on the above and foregoing, it can be appreciated that there presently exists a need in the art for a device which overcomes the above-described drawbacks and shortcomings of the presently available implantable cardiac stimulation device technology. The present invention fulfills this need.

SUMMARY OF THE INVENTION

The present invention encompasses a header adapter which is a separately molded part and which is designed to be secured to receiving portions of the header and pulse generator case of an implantable cardiac stimulation device, such as a pacemaker or implantable cardioverter-defibrillator, in order to provide a different lead connector port configuration and/or dimensions than that provided by the header of the device. The header adapter has a plurality of adapter lead connector ports and a plurality of lead connectors affixed to a rear portion (mounting side) thereof. The lead connectors extend outwardly from the rear portion of the header adapter, and are insertable into corresponding lead connector ports of the header of the implantable cardiac stimulation device to which the header adapter is to be secured. At least one of the plurality of adapter lead connector ports is of a different size than any of the header lead connector ports of the device to which the header adapter is to be secured, and/or the number of adapter lead connector ports is different (greater or less than) the number of header lead connector ports of the device to which the header adapter is to be secured. Two or more leads inserted into the header adapter lead connector ports can be electrically connected to the same lead connector and/or one or more of the leads inserted into a header adapter lead connector port(s) can each be electrically connected to two or more of the lead connectors. Further, one or more of the lead connectors can be an electrically inactive "dummy" lead connector. The header adapter is preferably made of a transparent or translucent polymeric or other electrically insulative, biocompatible material, such as an epoxy resin or thermoplastic elastomer.

In one embodiment of the invention, the header adapter couples two unipolar lead connectors and brings them to a single in-line bipolar connector. The header adapter may also provide one-to-one coupling of non-standard lead connectors to DF-1 standard adapter connectors.

The present invention also encompasses an implantable cardiac stimulation device to which the header adapter is secured. The header adapter is preferably sized to fit snugly over the receiving portions of the pulse generator case and header of the implantable cardiac stimulation device, and preferably has a shape which closely conforms to the contour of the receiving portions of the pulse generator case and header of the implantable cardiac stimulation device. Further, the header adapter connector ports are positioned to allow smooth "dressing" of leads around the contour of the pulse generator.

BRIEF DESCRIPTION OF THE DRAWINGS

The above and other objects, features, and advantages of the present invention will be more clearly understood from the following detailed description taken in conjunction with the accompanying drawings, in which.

DETAILED DESCRIPTION OF THE INVENTION

Figure 1:
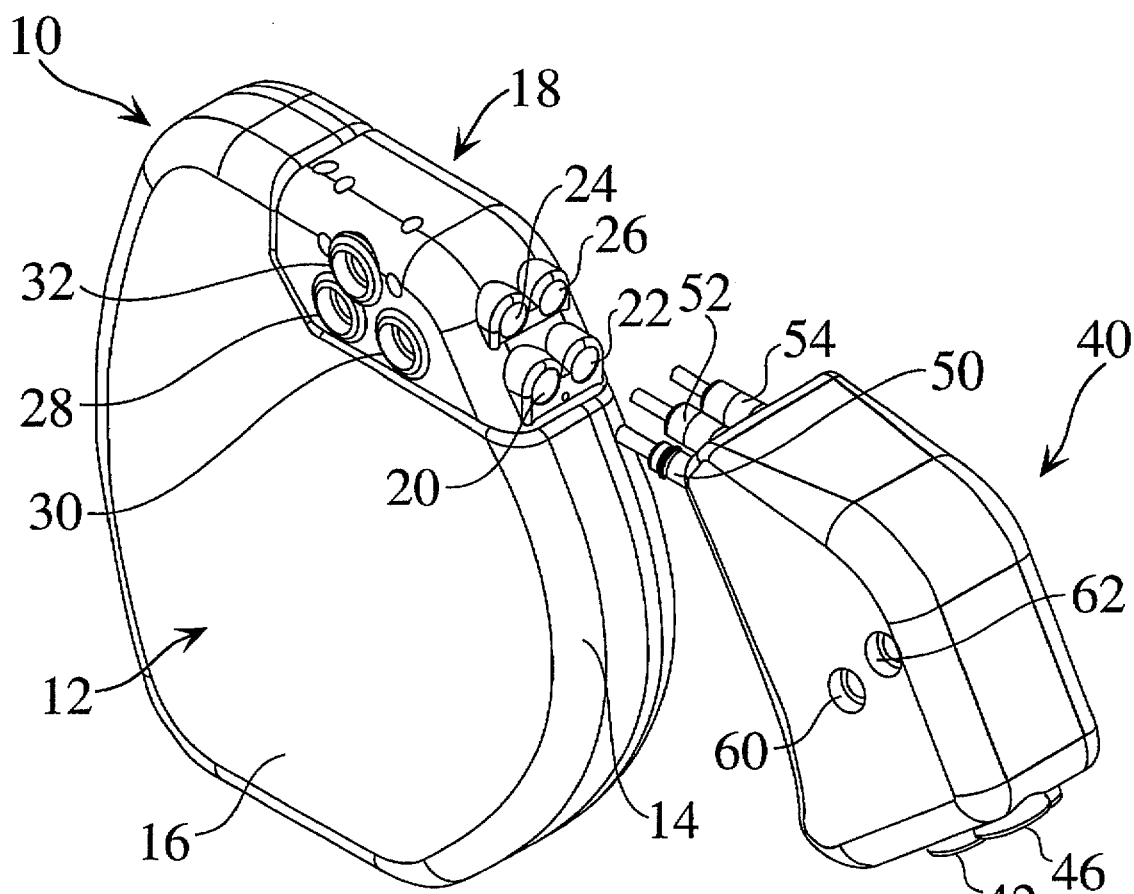
FIG. 1 is a perspective view of a header adapter constructed in accordance with a preferred embodiment of the present invention, and an implantable cardioverter-defibrillator onto which is designed to be installed.

With reference now to FIG. 1, there can be seen a standard implantable cardioverter-defibrillator (ICD) 10, in conjunction with which the header adapter of the present invention can be utilized. However, it should be clearly understood that the header adapter of the present invention can be utilized with any other type of implantable cardiac stimulation device, e.g., a pacemaker, the device 10 being shown and described herein for illustrative purposes only. The device 10 may conveniently be of the type which is capable of delivering tiered therapy, e.g., anti-bradycardia pacing therapy, anti-tachycardia pacing therapy, cardioversion therapy, and defibrillation therapy. For ease of description, the device 10 will hereinafter be referred to as the pulse generator 10. The housing 12 of the pulse generator 10 will hereinafter be referred to as the pulse generator case or can 12. The pulse generator can 12 houses the pulse generator circuitry (not shown) of the device, and is typically constructed of titanium, although any other corrosion-resistant, biocompatible electrically conductive material may be used instead. The pulse generator can 12 has a contour region 14 which will interface with the header adapter as discussed hereinbelow. The pulse generator can 12 may have an electrically conductive portion 16 which may serve as an electrode when the can is electrically activated. The surface of the pulse generator can 12 may be provided with an electrically insulative, polymeric coating (not shown) which serves to keep current flow between electrodes focused toward the heart during delivery of a defibrillation shock, so as to lower the defibrillation threshold (DFT) and to avoid undesirable skeletal muscle stimulation. The outer surface of the pulse generator can 12 may be of any desired shape or configuration to provide patient comfort and ease of implant. In this regard, the profile of the pulse generator is preferably made as thin as possible.

A header 18, which is preferably made of transparent or translucent polymeric material, such as an epoxy or thermoplastic elastomer is attached or secured to the can 12. It should be noted that the terms "attached" and "secured" are used hereinthroughout in their broadest possible sense, e.g., two parts can be attached or secured together by means of being press fit, welded, glued, or screwed together, or may be integrally formed or attached, e.g., machined from a unitary workpiece. The header 18 is provided with four lead connector cavities or ports 20, 22, 24, and 26, which can be thought of as tunnels or bores in the header 18. The header 18 is also provided with three threaded set screw holes or cavities 28, 30, and 32 on one side of the header 18, and two additional set screw cavities (not shown) opposite the set screw cavities 28 and 32, on the other side of the header 18. The set screw cavities 28, 30, and 32, (and those not shown) extend in a direction which is substantially transverse to the direction in which the lead connector ports 20, 22, 24, and 26 extend. The header 18 may obviously have a different number of connector cavities and set screw cavities. The set screw cavities 28, 30 and 32, (and those not shown) may contain an insulating septum at the cavity entrance. A set screw tool can be inserted through the septum to engage the electrically conductive set screw and then removed. The purpose of the septum is to electrically isolate the set screw from body fluids surrounding the pulse generator 10 and electrically conductive paths to other set screws, preventing electrical short circuits of defibrillator outputs and inputs.

Each of the lead connector ports 20, 22, 24, and 26 can be sized for reception of the lead connector of any suitable type and/or size of lead electrode. For example, the lead connector port 20 can be sized for reception of the lead connector of an in-line type bipolar pacing lead meeting the IS-1 standard, and the lead connector ports 22, 24, and 26 can be sized for reception of the lead connector of unipolar defibrillation leads meeting the DF-1 standard, e.g., KV, SVC, and SQ lead electrodes.

In this case, the IS-1 bipolar pacing lead (not shown) can be electrically activated at the time of device implantation by inserting or plugging the lead connector thereof into the lead connector port 20, and then tightening a first set screw (not shown) into the set screw cavity 28 and into contact with a tip electrode of the pacing lead, through a lead connector block (not shown) which is electrically connected to a first polarity (e.g., −) pacing voltage terminal of the pulse generator circuitry (not shown) of the pulse generator 10, and tightening a second set screw (not shown) into the set screw cavity 30 and into contact with a ring electrode of the pacing lead, through another lead connector block (not shown) which is electrically connected to a second polarity (e.g., +) pacing voltage terminal of the pulse generator circuitry (not shown) of the pulse generator 10.

At first one of the DF-1 unipolar defibrillation leads (not shown) can be electrically activated at the time of device implantation by inserting or plugging the lead connector thereof into the lead connector port 22, and tightening a set screw (not shown) into the set screw cavity (not shown) opposite the set screw cavity 28 and into contact with the lead connector pin thereof, through a connector block (not shown) which is electrically connected to a first polarity (e.g., +) high voltage output terminal of the pulse generator circuitry of the pulse generator 10. A second one of the DF-1 unipolar defibrillation leads can be electrically activated at the time of device implantation by inserting or plugging the lead connector thereof into the lead connector port 24, and then tightening a set screw (not shown) into the set screw cavity 32 and into contact with the lead connector pin thereof, through a connector block (not shown) which is electrically connected to the first polarity high voltage output terminal of the pulse generator circuitry of the pulse generator 10. A third one of the DF-1 unipolar defibrillation leads can be electrically activated at the time of device implantation by inserting or plugging the lead connector thereof into the lead connector port 26, and then tightening a set screw (not shown) into the set screw cavity (not shown) opposite the set screw cavity 32 and into contact with the lead connector pin thereof, through a connector block (not shown) which is electrically connected to a second polarity (e.g., −) high voltage output terminal of the pulse generator circuitry of the pulse generator 10.

Of course, this particular lead configuration is only illustrative, as any other suitable lead configuration can be employed by the implanting physician depending upon the requirements of the particular patient. For example, less than three defibrillator leads may be used. In this case, an electrically insulative, biocompatible plug(s) (not shown) is inserted into the unused lead connector port(s), in order to seal the port(s) against intrusion of bodily fluids, bacteria, and other contaminants.

It should be clearly understood that the header 18 may be provided with a lead connector port configuration different from the above-described exemplary lead connector port configuration. For example, the header 18 may be provided with two IS-1 pacing lead connector ports, and two DF-1 defibrillator lead connector ports, or any other desired number, types, and/or sizes of lead connector ports. However, prior to the advent of the present invention, whatever particular lead connector port configuration was chosen could not be changed or modified after the header 18 was molded onto the pulse generator can 12, except by using individual adapter(s) with any one or more of the lead connector ports to modify the effective connector and/or pin diameter (and possibly, the effective length/depth) thereof, in order to thereby modify the header to accommodate a lead(s) having a lead connector whose diameter is different than that of the unmodified (original) lead connector port(s). This may occur because the header connector ports are manufactured to a new standard or the header of a down-sized pulse generator is just too small to accommodate connector ports which fit old lead connectors. The various drawbacks, shortcomings, and limitations of using the presently available adapters were described hereinabove. The header adapter of the present invention described hereinbelow provides an alternative method of providing the pulse generator with a lead connector port configuration different than that provided by the header thereof, which overcomes the hereinabove described drawbacks, shortcomings, and limitations of the presently available adapters.

Figure 2:
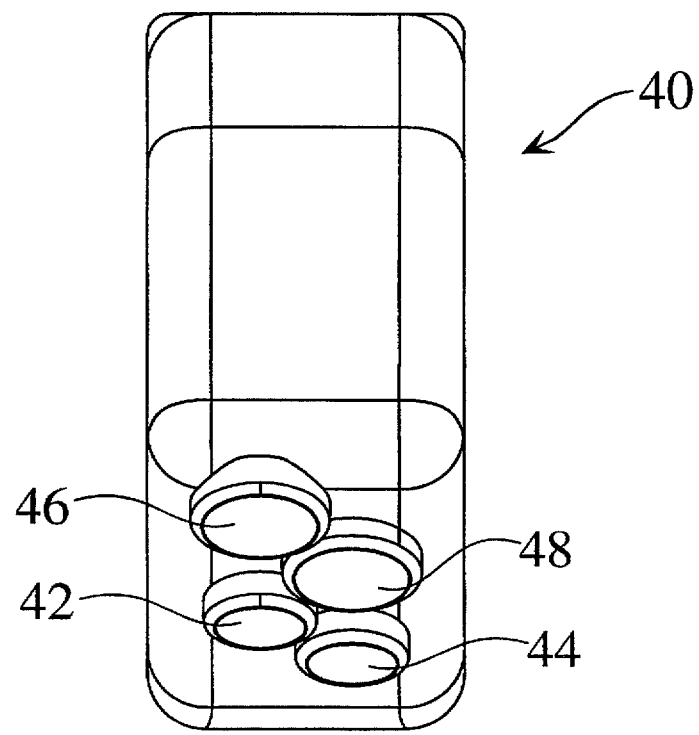
FIG. 2 is a frontal, elevational view of the header adapter of the present invention depicted in FIG. 1.
Figure 3:
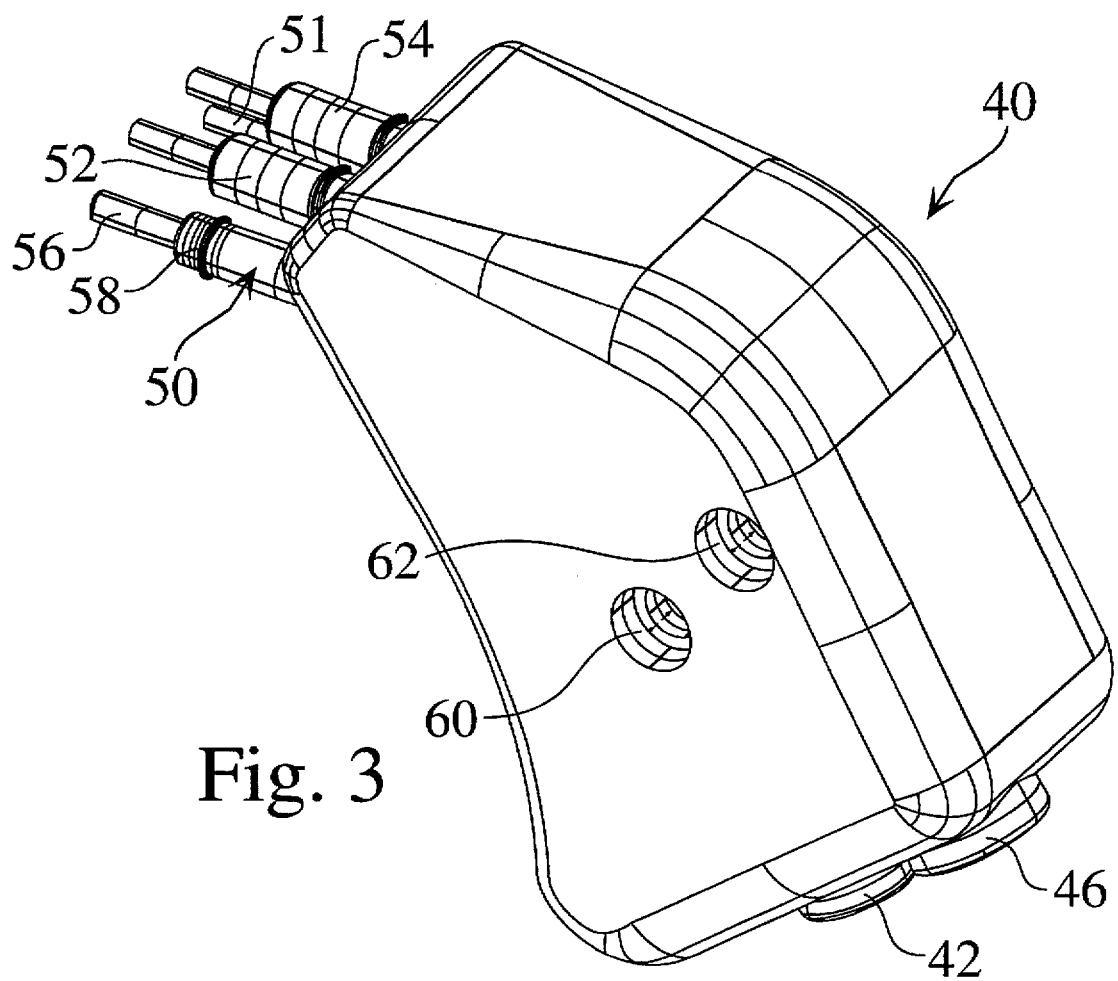
FIG. 3 is an enlarged, perspective view of the header adapter of the present invention depicted in FIGS. 1 and 2.

With reference now to FIGS. 1, 2, and 3 there can be seen different views of a header adapter 40 constructed in accordance with a preferred embodiment of the present invention. In overview, the header adapter 40 is a separately molded part which is designed to be secured to receiving portions of the header and pulse generator can of an implantable cardiac stimulation device, such as the pulse generator 10 described above and depicted in FIG. 1. The header adapter 40 is preferably made of a transparent or translucent polymeric or other electrically insulative, biocompatible material, such as an epoxy resin, a thermoplastic elastomer or other elastomeric material. Conveniently, the header adapter 40 can be made of the same material as is the header of the implantable cardiac stimulation device to which it is to be secured. The header adapter 40 of the present invention is preferably shaped to conform to the contour of the receiving portions of the header and pulse generator can of the implantable cardiac stimulation device to which it is to be secured, and is preferably sized to fit snugly over the receiving portions of the header and pulse generator can of the implantable cardiac stimulation device to which it is to be secured. However, the particular technique which is employed to secure the header adapter 40 to the implantable cardiac stimulation device is not limiting to the present invention. For example, the header adapter 40 may be glued, screwed, or otherwise attached or secured to the implantable cardiac stimulation device.

The basic purpose of the header adapter 40 of the present invention is to enable replacement pulse generators to be manufactured using the same header as new implants and accommodate previously implanted non-standard leads. In this connection, the header adapter 40 can be manufactured and sold separately for use by medical personnel (e.g., implanting physicians) at the time of device replacement, or it can be coupled to the pulse generator by the manufacturer as a final or near final manufacturing step.

With continuing reference to FIGS. 1, 2, and 3, the header adapter 40 of the preferred embodiment of the present invention is provided with four lead connector ports 42, 44, 46, and 48 formed in a front portion thereof, and four lead connectors 50, 51, 52, and 54 affixed to (e.g., molded into) a rear portion thereof. Preferably, the lead connectors 50, 51, 52, and 54 are potted in a compliant material, or mounted on a suspension system to allow them to flex, and thereby deflect and absorb shear forces and/or other mechanical forces, shocks, vibrations, and the like to which they may be subjected during the life of the pulse generator to which the header adapter 40 is secured. In addition, potting the four lead connectors 50, 51, 52 and 54 in a compliant material, or mounting them on a suspension system allows for misalignment between the four lead connectors and their respective lead connector ports 20, 22, 24 and 26. This system allows the header adapter 40 to be installed in the header 18 with lower required insertion force. It eliminates damaging misalignment forces that may be present in a rigid system that could create leaks with time. This system also prevents the transmission of a bending moment from a side force applied on header adapter 40 to the header 18. In a rigid system, there is a considerable moment distance, and the header 18 could easily be removed by a small force applied on the header adapter 40. This would be very undesirable. With the preferred embodiment, substantially all bending moments resulting from a side force on the header adapter 40 will be reacted on the surface of the can in region 14. The header adapter 40 is thus designed to closely fit this contour. The lead connectors 50, 51, 52, and 54 preferably extend laterally outwardly from the rear portion of the header adapter 40 in a direction substantially transverse to the axis of the lead connector ports 42, 44, 46, and 48. The header adapter 40 is also provided with two set screw cavities 60 and 62 formed in a first side portion of the header adapter 40, and two set screw cavities (not shown) formed in a second side portion of the header adapter 40 opposite the set screw cavities 60 and 62. Other connector fixation mechanisms known in the art, including the use of more than one set screw for each connector, could be used in either the header or the header adapter, and a different number of lead connector ports and lead connectors could be utilized depending upon the lead configuration and header configuration that are to be adapted.

In the illustrative embodiment, the lead connector ports 42 and 44 are unipolar type lead connector ports which are of a different size and configuration than the pacing lead connector port 20 oft he header 18 of the pulse generator 10 (e.g., in-line bipolar IS-1), and the lead connector ports 46 and 48 are lead connector ports which are of a different size than the defibrillator lead connector ports 22, 24, and 26 of the header 18 of the pulse generator 10 (e.g., unipolar DF-1). The lead connector 50 is an IS-1 type pacing lead connector having spaced-apart tip and ring electrodes 56 and 58, respectively, which is of the correct size to be plugged into the in-line bipolar pacing lead connector port 20 of the header 18 of the pulse generator 10, and the lead connectors 51, 52, and 54 are DF-1 type defibrillator lead connectors which are of the correct size to be plugged into the defibrillator lead connector ports 22, 24, and 26, respectively, of the header 18 of the pulse generator 10.

Thus, the pacing lead connector ports 42 and 44 of the header adapter 40 are sized to receive the lead connectors of pacing/sensing leads of a different size and configuration than the IS-1 pacing lead connector 50 and the corresponding pacing lead connector port 40 of the header 18, and the defibrillator lead connector ports 46 and 48 of the header adapter 40 are sized to receive the lead connectors of defibrillator leads of a different size than the DF-1 defibrillator lead connectors 51, 52, and 54 and the corresponding defibrillator lead connector ports 22, 24, and 26 of the header 18. In this embodiment, two unipolar pacing leads are brought together by the header adapter 40 from connector ports 42, 44 to a single in-line bipolar pacing/sensing IS-1 connector 50. Further, one of the DF-1 connectors (51, 52 or 54) of header adapter 40 is electrically inactive since only two defibrillation electrodes are used. Thus, by installing the header adapter 40 on the pulse generator 10 (in a manner more fully developed hereinafter), the lead connector port configuration of the pulse generator 10 can be changed from that of the header 18 to that of the header adapter 40, so that pacing/sensing leads and defibrillator leads of a different size (e.g., made by a different manufacturer) and configuration than those which would fit into the lead connector ports of the header 18 can be used by the implanting physician.

Figure 4:
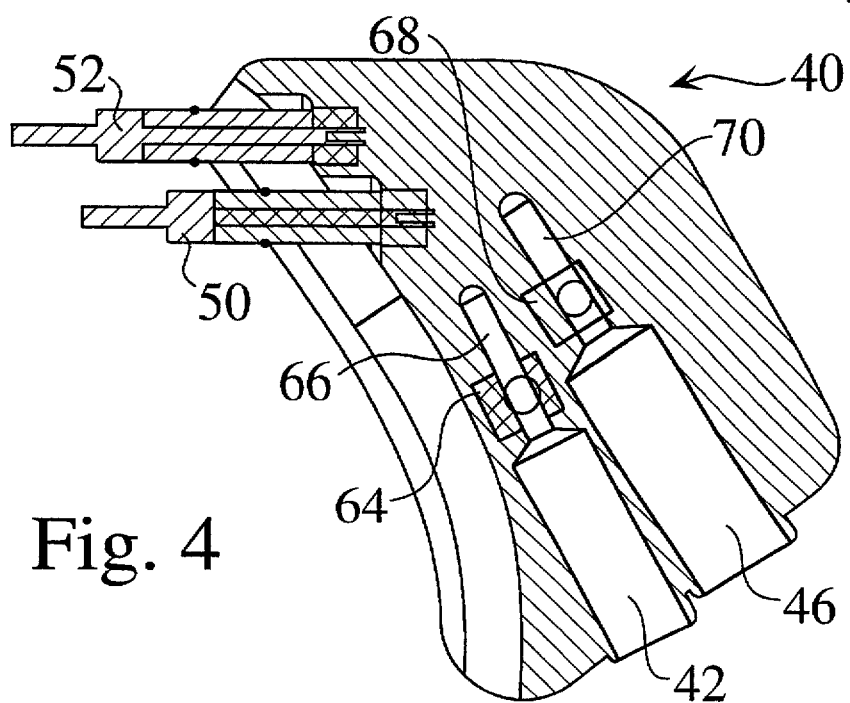
FIG. 4 is a cutaway, cross-sectional view of a portion of the header adapter of the present invention, depicted in FIGS. 1–3; and, FIG. 5 is a perspective view of the implantable cardioverter-defibrillator depicted in FIG. 1 with the header adapter of the present invention depicted in FIGS. 1–4 installed thereon.

With additional reference now to FIG. 4, the header adapter 40 is also provided with a standard lead connector block 64 disposed around a distal, connector pin receiving portion 66 of the lead connector port 42, and another lead connector block 68 disposed around a distal, connector pin receiving portion 70 of the lead connector port 46. Additional lead connector blocks (not shown) are provided around distal, connector pin receiving portions (not shown) of the lead connector ports 44 and 48, respectively. The lead connector block 64 and the lead connector block (not shown) opposite thereto, are both electrically connected to the lead connector 50, and the lead connector block 68 is electrically connected to the lead connector 52 in a manner well-known in the art, e.g., by electrical wires (not shown). The other lead connector block (not shown) is electrically connected to the lead connector 54 in a manner well-known in the art, e.g., by electrical wires (not shown). The lead connector 51 is not electrically connected to any of the lead connector blocks, and thus serves as a "dummy" lead connector which, when plugged into the corresponding lead connector port 22 of the header 18 of the pulse generator 10, will serve to seal the lead connector port 22 against intrusion of bodily fluids, bacteria, and other contaminants.

With reference now to FIGS. 1–4, the method of using the header adapter 40 to modify the lead connector port configuration of the pulse generator 10 will now be described, it being understood that the header adapter 40 of the present invention may also be employed in conjunction with any other suitable implantable cardiac stimulation device to modify the lead connector port configuration thereof. In order to secure the header adapter 40 to the pulse generator 10, the lead connector 50 is inserted into the corresponding lead connector port 20 of the header 18, the lead connector 51 is inserted into the corresponding lead connector port 22 of the header 18, the lead connector 52 is inserted into the corresponding lead connector port 24 of the header 18, the lead connector 54 is inserted into the corresponding lead connector port 26 of the header 18, and then the header adapter 40 is closely fitted onto the receiving portions of the pulse generator can 12 in the contour region 14 of the pulse generator 10.

Thereafter, the lead connector of a first unipolar type pacing/sensing lead (not shown) can be inserted into the lead connector port 42, the lead connector of a second unipolar type pacing/sensing lead (not shown) can be inserted into the lead connector port 44, the lead connector of a first defibrillator lead (not shown) can be inserted into the lead connector port 46, and the lead connector of a second defibrillator lead (not shown) can be inserted into the lead connector port 48.

The first unipolar type pacing/sensing lead can be electrically activated by tightening a first set screw (not shown) into the set screw cavity 28 of the header 18 and into contact with the tip electrode 56 of the lead connector 50 through the corresponding lead connector block (not Shown), and then tightening a second set screw (not shown) into the set screw cavity 60 of the header adapter 40 and into contact with a connector tip portion (not shown) of the first unipolar type pacing/sensing lead through the lead connector block 64. The second unipolar type pacing/sensing lead can then be electrically activated by tightening a third set screw (not shown) into the set screw cavity 30 of the header 18 and into contact with the ring electrode 58 of the lead connector 50 through the corresponding lead connector block (not shown) and then tightening a fourth set screw (not shown) into the set screw cavity (not shown) of the header adapter 40 which is opposite the set screw cavity 60, and into contact with a connector tip portion (not shown) of the second unipolar type pacing/sensing lead through the lead connector block (not shown) opposite the lead connector block 64. The set screw cavities 60 and 62 in the header adapter 40 may contain insulating septums such as those discussed above with reference to the header 18 to electrically isolate the set screws from body fluids surrounding the pulse generator 10 and electrically conductive paths to other set screws, preventing electrical short circuits of defibrillator outputs and inputs.

The first defibrillator lead can be electrically activated by tightening a fifth set screw (not shown) into the set screw cavity 32 of the header 18 and into contact with the lead connector pin portion of the lead connector 52, through the corresponding lead connector block (not shown), and then tightening a sixth set screw (not shown) into the set screw cavity 62 of the header adapter 40, and into contact with the lead connector pin portion of the first defibrillator lead through the lead connector block 68.

The second defibrillator lead can be electrically activated by tightening a seventh set screw (not shown) into the set screw cavity (not shown) of the header 18 opposite the set screw cavity 32, and into contact with the lead connector pin portion of the lead connector 54, through the corresponding lead connector block (not shown), and then tightening an eighth set screw (not shown) into the set screw cavity (not shown) of the header adapter 40 opposite the set screw cavity 62, and into contact with the lead connector pin portion of the second defibrillator lead through the lead connector block (not shown) opposite the lead connector block 68.

Finally, a ninth set screw (not shown) is tightened into the set screw cavity (not shown) of the header 18 opposite set screw cavity 30, and into contact with the lead connector pin portion oft he lead connector 51, through the corresponding lead connector block (not shown). Lead connector 51 is not electrically connected to any leads but is used to provide mechanical stability.

Each of the lead connectors 50, 51, 52 and 54 includes one or more O-rings to provide a fluid-tight seal in each of connector ports 20, 22, 24, 26 of header 18 in a manner well known in the art.

Figure 5:
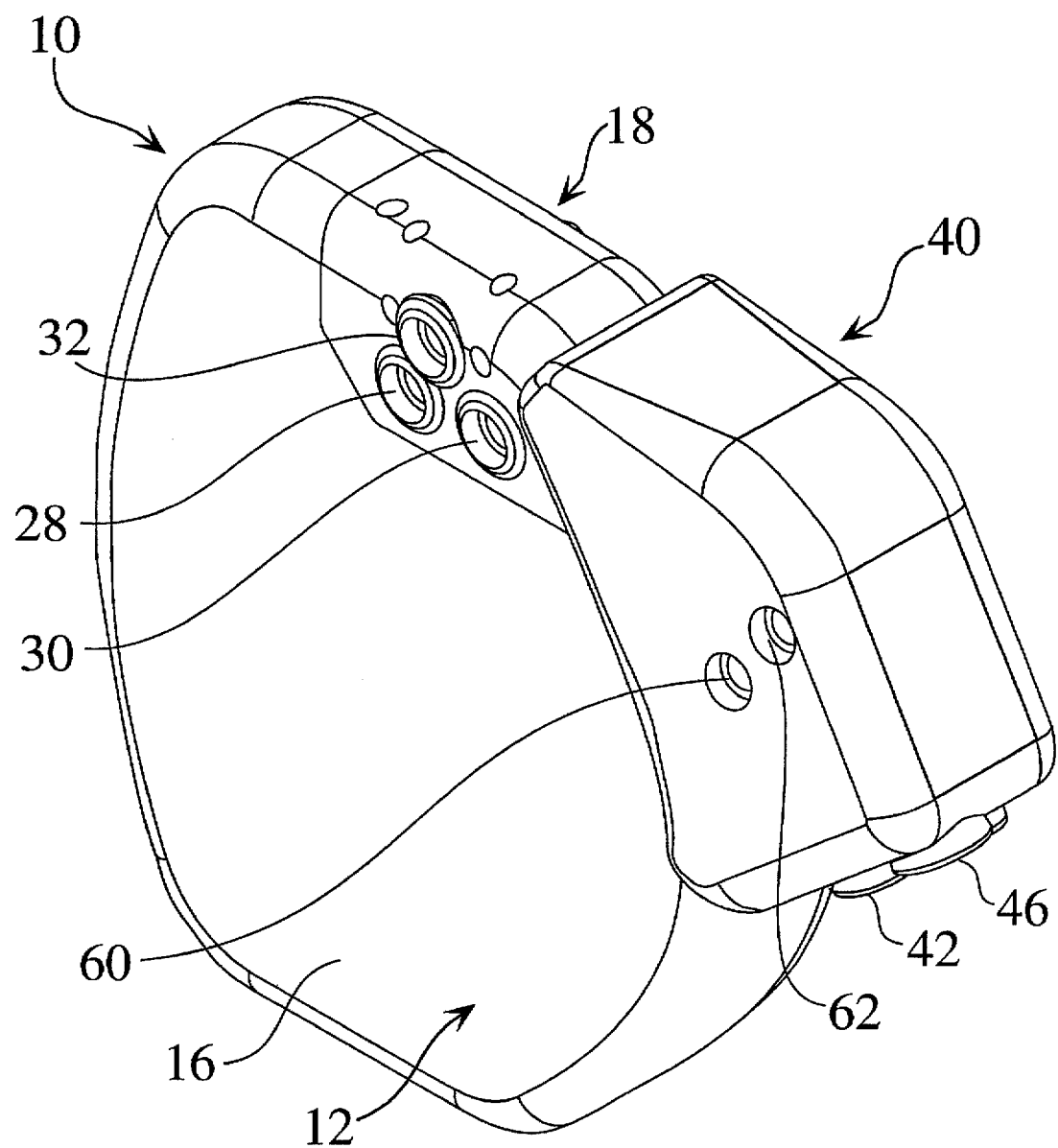

With reference now to FIG. 5, there can be seen the pulse generator 10 having the header adapter 40 installed thereon. As can be easily seen, the header adapter 40 covers the lead connector ports 20, 22, 24, and 26 of the header 18 and appears to be an extension of the header 18. In this regard, the header 18 and the header adapter 40 can be considered to together comprise a header assembly. Further, as will be readily appreciated by those skilled in the pertinent art, the engaging surfaces of the header adapter 40 and the pulse generator 10 preferably form a tight seal to minimize or prevent seepage of bodily fluids, bacteria, and other contaminants therebetween.

As previously mentioned, there are a large number of possible embodiments of the header adapter of the present invention other than the specific one described herein by way of illustration. For example, if the pulse generator has two unipolar pace/sense lead connector ports of a first size, and it is desired to use a single bipolar pace/sense lead of a second size, the header adapter could be provided with a single bipolar pace/sense lead connector port of the second size, and two unipolar lead connectors of the first size. As another example, if the pulse generator has two defibrillation lead connector ports, and it is desired to use three defibrillation leads, then the header adapter could be provided with three defibrillation lead connector ports of the appropriate size (which may or may not be different than the size of the defibrillation lead connector ports of the header of the pulse generator), and two defibrillation lead connectors of the appropriate size to be plugged into the defibrillation lead connector ports of the header of the pulse generator, with two of the defibrillation leads being electrically connected (via corresponding lead connector blocks and electrical conductors) to the same defibrillation lead connector.

In general, although a presently contemplated, illustrative embodiment of the present invention has been described in detail hereinabove, it should be clearly understood that many variations and/or modifications of the basic inventive concepts herein taught which may appear to those skilled in the pertinent art will still fall within the spirit and scope of the present invention, as defined in the appended claims.

What is claimed is:

1. A header adapter which can be secured to an implantable cardiac stimulation device having a pulse generator case and a header provided with a plurality of header lead connector ports, the header adapter comprising:

a member having a plurality of adapter lead connector ports; and, a plurality of lead connectors affixed to a rear portion of said member and extending outwardly therefrom, said lead connectors being insertable into corresponding ones of the header lead connector ports of the implantable cardiac stimulation device to which the header adapter is to be secured.

2. The header adapter as set forth in claim 1, wherein the number of said adapter lead connector ports is greater than the number of header lead connector ports of the implantable cardiac stimulation device to which the header adapter is to be secured.

3. The header adapter as set forth in claim 1, wherein the number of said adapter lead connector ports is less than the number of header lead connector ports of the implantable cardiac stimulation device to which the header adapter is to be secured.

4. The header adapter as set forth in claim 1, wherein said member is sized to fit snugly over receiving portions of the header and pulse generator case of the implantable cardiac stimulation device to which the header adapter is to be secured.

5. The header adapter as set forth in claim 1, wherein two of said lead connector ports of said member are adapted to receive unipolar lead connectors and one of said plurality of lead connectors of said member is an in-line bipolar connector coupled within said member to said two unipolar lead connectors ports.

6. The header adapter as set forth in claim 1, wherein one of said lead ports of said member is adapted to receive an in-line bipolar connector and two of said plurality of lead connectors of said member are unipolar connectors coupled within said member to said in-line bipolar connector.

7. The header adapter as set forth in claim 1, wherein the number of said adapter lead connector ports is the same as the number of header lead connector ports of the implantable cardiac stimulation device to which the header adapter is to be secured and at least one of said adapter lead connector ports has a different size from a corresponding one of said header lead connector ports.

8. The header adapter as set forth in claim 1, wherein said member has a shape which closely conforms to the contour of receiving portions of the header and pulse generator case of the implantable cardiac stimulation device to which the header adapter is to be secured.

9. The header adapter as set forth in claim 8, wherein said member is sized to fit snugly over receiving portions of the header and pulse generator case of the implantable cardiac stimulation device to which the header adapter is to be secured.

10. The header adapter as set forth in claim 1, wherein at least one of said plurality of adapter lead connector ports is of a different size than any of the header lead connector ports of the implantable cardiac stimulation device to which the header adapter is to be secured.

11. The header adapter as set forth in claim 10, wherein said member is made of an electrically insulative, biocompatible material.

12. The header adapter as set forth in claim 11, wherein said electrically insulative, biocompatible material is selected from a group consisting of epoxy, polyurethane, and silicone rubber.

13. The header adapter as set forth in claim 1, wherein:
each of said lead connector ports of said member extends longitudinally from a front surface of said member and terminates within said member; and,
each of said lead connector ports of said member has a distal, lead connector pin receiving portion.

14. The header adapter as set forth in claim 13, further comprising a plurality of lead connector blocks disposed about corresponding ones of said lead connector pin receiving portions of said lead connector ports of said member.

15. The header adapter as set forth in claim 14, wherein the number of said adapter lead connector ports is greater than the number of header lead connector ports of the implantable cardiac stimulation device to which the header adapter is to be secured.

16. The header adapter as set forth in claim 15, wherein the number of said adapter lead connector ports is greater than the number of said lead connectors.

17. The header adapter as set forth in claim 14, wherein the number of said adapter lead connector ports is less than the number of header lead connector ports of the implantable cardiac stimulation device to which the header adapter is to be secured.

18. The header adapter as set forth in claim 17, wherein the number of said adapter lead connector ports is less than the number of said lead connectors.

19. The header adapter as set forth in claim 14, wherein at least two of said lead connector blocks are electrically connected to respective ones of said lead connectors.

20. The header adapter as set forth in claim 19, further comprising a plurality of set screw cavities formed in said member, each of said set screw cavities extending transversely from a side surface of said member to a respective one of said lead connector blocks.

21. The header adapter as set forth in claim 19, wherein at least one of said lead connectors is not electrically connected to any of said lead connector blocks.

22. The header adapter as set forth in claim 19, wherein at least two of said lead connector blocks are electrically connected to the same one of said lead connectors.

23. An implantable cardiac stimulation device, comprising:
a pulse generator case housing pulse generator circuitry;
a header secured to said pulse generator case, said header being provided with a plurality of header lead connector ports and corresponding transversely disposed set screw cavities;
a header adapter having a plurality of adapter lead connector ports extending from a front surface of said header adapter and terminating within said header adapter, a plurality of corresponding transversely disposed set screw cavities, and a plurality of lead connectors affixed to a rear portion of said header adapter and inserted into corresponding ones of said header lead connector ports; and,
wherein said header adapter is secured to receiving portions of said pulse generator case and said header.

24. The implantable cardiac stimulation device as set forth in claim 23, wherein the number of said adapter lead connector ports is different than the number of header lead connector ports.

25. The implantable cardiac stimulation device as set forth in claim 23, wherein at least one of said plurality of adapter lead connector ports is of a different size than any of said header lead connector ports.

26. The implantable cardiac stimulation device as set forth in claim 25, wherein the number of said adapter lead connector ports is different than the number of header lead connector ports.

27. The implantable cardiac stimulation device as set forth in claim 23, wherein said header adapter is sized to fit snugly over said receiving portions of said pulse generator case and said header.

28. The implantable cardiac stimulation device as set forth in claim 27, wherein said header adapter has a shape which closely conforms to the contour of said receiving portions of said pulse generator case and said header.

* * * * *